United States Patent [19]

Kotaka et al.

[11] 4,157,470
[45] Jun. 5, 1979

[54] INFRARED GAS ANALYZER

[75] Inventors: Mitsuo Kotaka; Hisao Takahara; Kaisuke Muraki; Ryo Takahashi; Tamizo Matsuura, all of Musashino, Japan

[73] Assignee: Yokogawa Electric Works, Ltd., Tokyo, Japan

[21] Appl. No.: 888,223

[22] Filed: Mar. 20, 1978

[30] Foreign Application Priority Data

Mar. 24, 1977 [JP] Japan .................................. 52-32432
Mar. 25, 1977 [JP] Japan ............................. 52-36767[U]
Nov. 18, 1977 [JP] Japan ................................ 52-139095

[51] Int. Cl.² .......................................... G01N 21/26
[52] U.S. Cl. .................................... 250/345; 250/346
[58] Field of Search ................ 250/343, 344, 345, 346

[56] References Cited

U.S. PATENT DOCUMENTS 2,999,929  9/1961  Martin et al. ......................... 250/345
3,193,676  7/1965  Smart .................................... 250/345

*Primary Examiner*—Davis L. Willis
*Attorney, Agent, or Firm*—Parmelle, Johnson, Bollinger & Bramblett

[57] ABSTRACT

To detect the density of a measurement component of a sample gas, infrared light is directed alternately through a measuring-light optical system and a reference-light optical system to a heated light sensor. The measuring-light optical system includes a sample cell, a first filter for transmitting infrared rays of a fixed wave-length band, and a temperature compensating cell having a gas which has a part of its absorption wave-length band within the transmission wave-length band of the first filter but has a spectrum different from the spectrum of the measurement component. The reference-light optical system includes a light throttle, an interference cell having a gas containing a fixed density of the measurement component, an adjustable-length interference compensating cell filled with the sample gas, and a second filter for transmitting rays of a wave-length band that includes the major part of the transmission wave-length band of the first filter. The compensating cell is set such that, with temperature fluctuations, variations in absorption by the temperature compensating cell in the wave-length band of the first filter are equal to variations in absorption by the interference cell within the wave-length band of the second filter.

8 Claims, 8 Drawing Figures

# INFRARED GAS ANALYZER

CROSS REFERENCE TO A RELATED APPLICATION

The commonly assigned and copending U.S. Patent Application by Kotako et al entitled Detector For Use In Infrared Gas Analyzer.

BACKGROUND OF THE INVENTION

The present invention relates to an infrared gas analyzer for analyzing components in a gas by utilizing absorption of infrared rays, and more particularly to an improved analyzer which performs analysis on an introduced sample gas containing an interference component as well as a measurement component.

Where infrared analyzers are used to determine the concentration of a measurement component in a gas sample, there is often an interference component of the sample whose absorption wave-length band overlaps that of the measurement component. To avoid measurement errors due to the interference component, it is necessary to make some proper compensation for that component. One of the methods adopted heretofore in conventional apparatus includes measuring the density of the interference component separately and then executing computations to obtain the density of the measurement component. However, it is unavoidable that an apparatus based on such a method becomes undesirably complicated.

The present invention has been accomplished in view of the above circumstances, and its object is to provide an improved infrared gas analyzer of simple structure which eliminates influence resulting from the existence of an interference component and further achieves reduction of variations caused by ambient temperature fluctuation.

SUMMARY OF THE INVENTION

According to the invention in one of its aspects, a measuring-light optical system comprises a sample cell, a first filter for principally transmitting infrared rays of a fixed wave-length band included within the absorption wave-length band of a measurement component, and a temperature compensating cell enclosing therein a gas which has a part of its absorption wave-length band within the transmission wave-length band of the first filter but is different in spectrum from the measurement component. A reference-light optical system comprises an interference compensating cell, a second filter for transmitting infrared rays of such a wave-length band that includes the major part of the transmission wave-length band of the first filter, and an interference cell enclosing therein a gas containing a measurement component of a fixed density.

According to the invention in another of its aspects, the interference cell is hermetically inserted into one end of the interference compensating cell and is movable therein so as to allow for easy adjustment of the length of the interference compensating cell.

According to the invention in yet another of its aspects, the analyzer includes an improved detector wherein a light sensor and a multilayer interference filter are associated with a metallic block, and the temperature of the metallic block is maintained constant so as to protect the light sensor and the multilayer interference filter from the undesirable influence of ambient temperature fluctuation.

DESCRIPTION OF PREFERRED EMBODIMENTS

Figure 1:
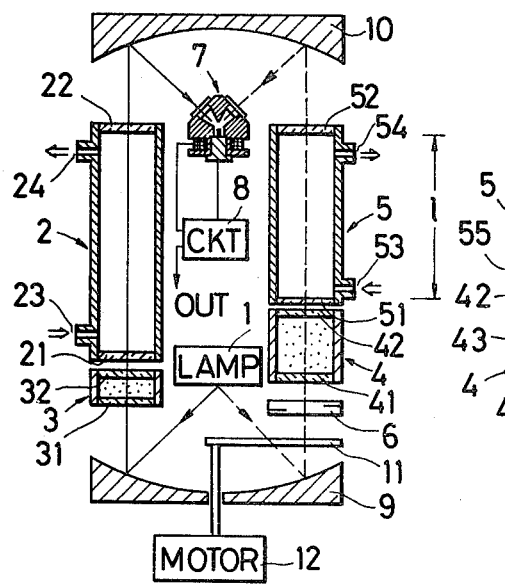
FIG. 1 is a sectional view illustrating the structure of an infrared gas analyzer embodying the present invention.

An embodiment of an infrared gas analyzer according to this invention and shown in FIG. 1 includes an infrared-ray source 1 and a sample cell 2 filled with a sample gas. The sample cell 2 has an inlet port 23 and an outlet port 24 for introducing and exhausting the sample gas. A temperature compensating cell 3 enclosing a gas therein has windows 31, 32 for transmission of infrared rays.

Figure 7:
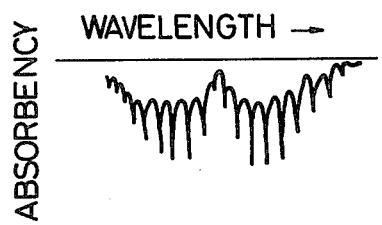
FIG. 7 is a graphic representation of an exemplary vibration and rotation spectrum of a gas.

The gas enclosed in the temperature compensating cell has an absorption wave-length band that is partially included within the transmission wave-length band of a filter 74 (which will be described afterward) but is different in spectrum from a measurement component of the sample gas. Since gaseous molecules are freely rotatable, a change in the state of vibration is always accompanied with a change in the state of rotation, so that a vibratory spectrum appears with a rotatory spectrum, both of which are shown for an exemplary gas in FIG. 7. As shown in FIG. 7, the spectrum within a wavelength band includes a group of spectral lines termed positive branch and negative branch. The gas enclosed in the temperature compensating cell 3 may be such that it is fundamentally similar in spectrum to the measurement component but is different therefrom with respect to the group of spectral lines. (It is possible to select, for example, $C_2H_4$ as the above gas when the measurement component is NO.)

A reference system includes an interference cell 4 having therein a gas which contains a measurement component of a fixed density, and an interference compensating cell 5 filled with a sample gas. The interference cell 4 has windows 41, 42 for transmission of infrared rays, and the interference compensating cell 5 has windows 51, 52 for transmission of infrared rays. The cell 5 also has an inlet port 53 and an outlet port 54 for introducing and exhausting the sample gas.

Figure 2:
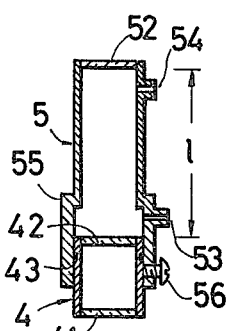
FIGS. 2 and 3 are sectional views of alternative interference compensating cells for use in the analyzer of FIG. 1.
Figure 3:
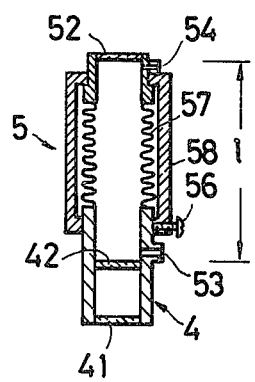

Desirably the interference compensating cell 5 is so constructed that its length l is easily adjustable in an analyzer calibrating operation which will be described afterward. Preferred examples of such an adjustable cell are shown in FIGS. 2 and 3. In the interference compensating cell 5 of FIG. 2, a window 52 is formed at one end for transmitting infrared rays, and the other end is shaped into an outer cylinder 55 where the interference cell 4 is inserted. The length l of the interference compensating cell 5 is changed by adjusting the insertion distance of the interference cell 4 in the outer cylinder 55; that distance is fixed by a set screw 56. An O-ring 43 is embedded in a groove formed around the outer surface of the interference cell 4 in the vicinity of window 42, and serves to prevent leakage of the gas filling the interference compensating cell 5.

In the example of FIG. 3, the interference compensating cell 5 is partially composed of a bellows 57. A cylinder including interference cell 4 is held firmly in a hollow sleeve 58 by a set screw 56 to fix the length 1 of the interference compensating cell 5.

With reference to FIG. 1 again, a throttle 6, the interference cell 4 and the interference compensating cell 5 are disposed coaxially with one another; and the sample cell 2 and the temperature compensating cell 3 are disposed coaxially with each other. A detector 7 receives infrared light and transmits an electric signal to a signal converter/temperature controller 8. The detector 7 is located near the focal point of a concave reflex mirror 10 to receive intermittent light after the light has passed through the sample cell 2, the interference cell 4 and so forth. The intermittent light emitted from the infrared-ray source 1 is first formed into parallel rays by the concave reflex mirror 9. Then, the parallel rays pass through an interrupter 11 rotated by a motor 12.

Figure 4:
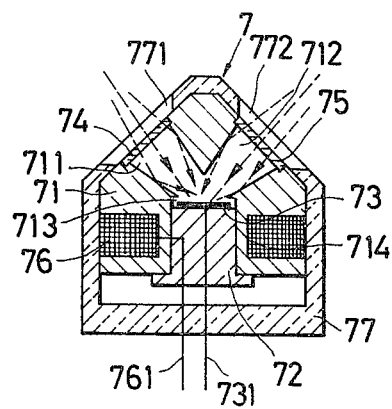
FIG. 4 is a sectional view of a detector for use in the analyzer of FIG. 1.
Figure 5:
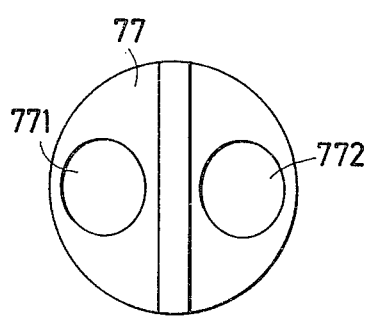
FIG. 5 is a plan view of the detector of FIG. 4.

Now a further detailed explanation of the detector 7 and the signal converter/temperature controller 8 will be given with reference to FIGS. 4 through 6. FIG. 4 is a sectional view of the detector 7 illustrating the structure thereof, and FIG. 5 is its plan view. A metallic block 71 has a conical measuring-light inlet port 711 and a conical reference-light inlet port 712 for accepting the measuring light and the reference light respectively. A light-sensor mounting hole 713 is formed at the intersection of the light inlet ports 711, 712 of the metallic block 71. A base plate 72 is inserted into and fixed within the mounting hole 713 of the metallic block 71, and a light sensing element such as thermistor-bolometer is secured onto the base plate 72. A wire 731 serves to connect the light sensing element 73 to the signal converter/temperature controller 8. A multilayer interference filter 74 is attached to the metallic block 71 to close the measuring-light inlet port 711, and a multilayer interference filter 75 is also attached to the metallic block 71 to close the reference-light inlet port 712. Each of the interference filters is so positioned as to face the incoming light related thereto. The space formed by the light inlet ports 711, 712 and the mounting hole 713 is maintained in a completely hermetic state and is filled with nitrogen gas $N_2$.

A heater 76 is disposed in a ring-shaped groove 714 formed on the outer surface of the metallic block 71. The heater 76 heats the metallic block 71. A connecting wire 761 feeds an output of the signal converter/temperature controller 8 to the heater 76.

The entire metallic block 71 is coated with a member 77 composed of, for example, bakelite resin. Due to the coating member 77, the metallic block 71 is effectively shielded from ambient temperature. A window 771 for the measuring-light inlet port 711, and a window 772 for the reference-light inlet port 712 are provided in the coating member 77.

Figure 6:
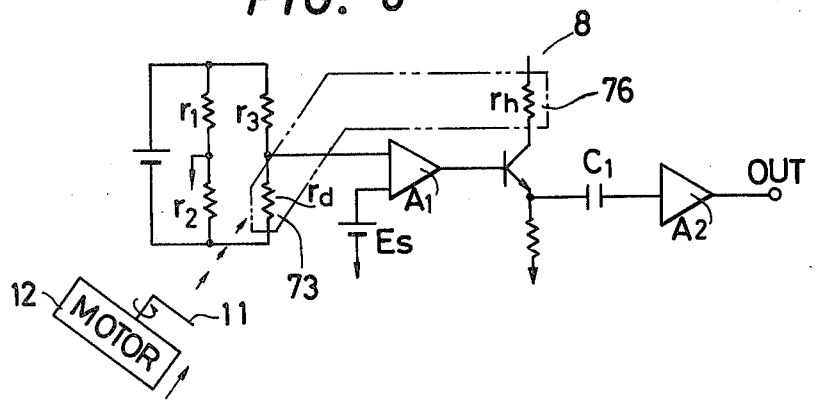
FIG. 6 is a circuit diagram of a signal converter/temperature controller for use in the analyzer of FIG. 1.

In the circuit configuration of signal converter/temperature controller 8 shown in FIG. 6, the thermistor-bolometer 73 represented by $r_d$ is regarded as a resistance element. This element is combined with other resistance elements r1, r2, r3, stable to temperature, and a d-c power source Eo to constitute a bridge circuit which receives the measuring light and the reference light intermitted by the interrupter 11. The difference between the unbalanced voltage of the bridge circuit and a preset voltage Es is amplified by a low-noise amplifier A1 of high input impedance and is further amplified by a transistor Q1, the output current of which energizes the heater 76 (resistance element $r_h$). Simultaneously, the a-c component alone of the output current is fed through a capacitor C1 to an amplifier A2 so that a measurement signal is obtained from the output terminal OUT thereof.

The infrared gas analyzer of the above-described structure performs its operation as follows. The output of the detector 7 fed to the signal converter/temperature controller 8 is composed of two information signals. One is an a-c measurement signal representing the measurement component of the sample gas. This signal is obtained by intermitting by the interrupter 11 the light emitted from the infrared-ray source 1, and then introducing the light to the detector 7 via the sample cell 2 and the interference cell 4. And the other signal represents the temperature of the thermistor-bolometer 73 resulting from heating of the metallic block 71 by the heater 76. The former signal indicates a-c changes of a short period, while the latter indicates d-c changes with a slow response due to a large time constant of the heater. Accordingly, the output signal of the bridge circuit consisting of the resistance element rd, r1, r2, r3 and the power source Eo is formed of the d-c component and the a-c component superposed thereon. And the difference between this signal and the preset voltage Es is amplified by both the amplifier A1 and the transistor Q1 to produce an output signal to energize the heater 76, thereby controlling the thermistor-bolometer 73 to maintain a temperature corresponding to the preset voltage Es. In this control system, the a-c component causes no harmful effect since the time constant of the heater 76 is great. On the other hand, the superposed a-c component of the signal is passed through capacitor C1 and further amplified by the amplifier A2 to produce a measurement signal, the magnitude of which is determined by the physical properites of the transmission light path. This relationship will be described in more detail below.

Figure 8:
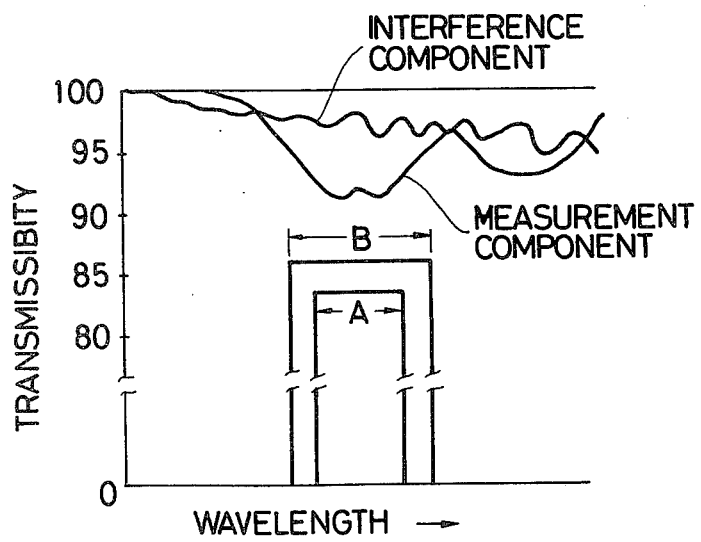
FIG. 8 is a graphic representation of absorption characteristics of the measurement and interference components of a gas and of interference filters used in the analyzer of FIG. 1.

In the analyzer of the structure shown in FIG. 1, a gas to be analyzed is presumed to contain a measurement component and an interference component having such absorbency as graphed in FIG. 8, where a group of spectral lines is omitted for clarity of illustration. Here, the filter 74 has the wave-length band A of FIG. 8, and the filter 75 has the wave-length band B.

When the interrupter 11 is located on the side of the interference cell 4 as shown in FIG. 1, the light emitted from the infrared-ray source 1 advances through a path formed of concave reflex mirror 9, temperature compensating cell 3, sample cell 2, concave reflex mirror 10, filter 74, and thermistor-bolometer 73. Accordingly, the quantity of light Lm arriving at the thermistor-bolometer 73 is expressed as $$Lm = Lom - (Lxm + Lim + Ltm) \tag{1}$$

in which

Lom: quantity of light arriving at thermistor-bolometer 73 after passing through sample cell 2, temperature compensating cell 3 and filter 74 on the assumption that these two cells enclose therein a gas having no absorption wave-length band within the band A.

Lxm: reduction of Lom caused by the measurement component of the gas actually in sample cell 2.

Lim: reduction of Lom caused by the interference component of the gas actually in sample cell 2.

Ltm: reduction of Lom caused by the gas actually in temperature compensating cell 3.

When the interrupter 11 rotates 180° from the position shown in FIG. 1, the infrared light emitted from the infrared-ray source 1 advances through a path formed of concave reflex mirror 9, throttle 13, interference cell 4, interference compensating cell 5, concave reflex mirror 10, filter 75 and thermistor-bolometer 73. Accordingly, the quantity of light Lr arriving at thermistor-bolometer 73 is expressed as $$Lr = Lor + (Lxr + Lir + Ltr) \quad (2)$$

in which

Lor: quantity of light arriving at thermistor-bolometer 73 after passing through interference cell 4, interference compensating cell 5 and filter 75 on the assumption that these two cells enclose therein a gas having no absorption wave-length band within the band B.

Lxr: reduction of Lor caused by the measurement component of the gas actually in interference compensating cell 5.

Lir: reduction of Lor caused by the interference component of the gas actually in interference compensating cell 5.

Ltr: reduction of Lor caused by the gas actually in interference cell 4 including a measurement component of fixed density.

From the above equations (1) and (2), the difference $\Delta L$ between the quantities of light arriving at the thermistor-bolometer 73 is obtained by $$\Delta L = Lm - Lr = Lo - Lx - Li - Lt \quad (3)$$

in which
Lo = Lom − Lor
Lx = Lxm − Lxr
Li = Lim − Lir
Lt = Ltm − Ltr

As will be apparent from a later discussion of the calibration of the analyzer, Lx is the quantity indicating the density of the measurement component in the sample gas. $\Delta L$ is the quantity corresponding to the output amplitude (a-c component) of the detector 7, that is, the signal amplified by the amplifier A2 through the capacitor C1 of the signal converter/temperature controller 8. When the analyzer is properly calibrated as set forth below, the parameters Lo, Li, and Lt are held constant; thus the output $\Delta L$ is proportional to Lx.

An explanation will now be given on how to calibrate the gas analyzer of this invention. The temperature compensating cell 3 is used for the purpose of avoiding a temperature error that results from the provision of the interference cell 4. The length of the temperature compensating cell 3 and the density of the gas enclosed therein are so adjusted that the variation of Ltm caused by temperature fluctuation is equal to the variation of Ltr. Since the gas in each of the interference cell 4 and the temperature compensating cell 3 remains unchanged, Lt is maintained at a fixed value Ca independently of temperature fluctuation.

Calibration for eliminating the influence of the interference component in the sample gas is performed according to the following procedure. First, a gas such as nitrogen without infrared absorption is supplied as a sample gas, and the throttle 6 is adjusted so that the amplitude of the light quantity incident upon the detector 7 becomes zero or a fixed value Cb. (Since this adjustment is not wide, there is no problem that Lt is varied by temperature fluctuation.) Since Lx and Li at this point equal zero, this adjustment provides for Lo − Lt = 0 or Lo − Lt = Cb. Next, a gas containing an interference component but no measurement component is supplied as a sample gas, and the length 1 of the interference compensating cell 5 is adjusted so that the amplitude of the light quantity incident upon the detector 7 becomes zero or a fixed value Cb. Thus, this adjustment provides for Li = 0. The difference $\Delta L$ after such calibration is expressed as $$\Delta L = -Lx \text{ or } \Delta L = Cb - Lx \quad (4)$$

Consequently, if the density of the interference component contained in the sample gas is varied, Lx proportional to the measurement component density is still obtainable accurately from the output amplitude of the dectector 7. Moreover, as the influence of temperature fluctuation on the interference cell 4 is eliminated by the provision of the temperature compensating cell 3, there is no necessity of incorporating the interference cell 4 and so forth in a thermostatic oven. Furthermore, by virtue of attaching the filters 74, 75 to the detector 7 in the condensing part, the filters 74, 75 can be shaped in small dimensions, and temperature control for the detector 7 and that for the filters 74, 75 are simultaneously achievable with ease. Therefore, the above embodiment advantageously does not require a thermostatic oven.

Although merely one example is shown for the disposition sequence of the cells and so forth, it is of course possible to attain equal effects by other sequences of the analyzer components as well. The filter having the wave-length band B that includes the entire wave-length band A of the measuring-light filter is located on the reference-light side. However, equal effects are also attainable if the two wave-length bands otherwise overlap each other in the major parts thereof. Locating the throttle and so forth on the side of the sample cell is rendered possible by proper selection of the wave-length bands A and B.

Furthermore, the thermistor-bolometer used as a light sensor and heated in the foregoing embodiment may be replaced with some other element such as a photoconductive cell (TLS, PbS, CdS, etc.), and the structure may be so modified as to cool such element. One of cooling means available is a low-temperature stabilizer equipped with a Peltier-effect element.

According to the present invention, as described hereinabove, it becomes possible to realize an improved infrared gas analyzer of simple structure which is capable of automatically eliminating the influence of an interference component.

We claim:

1. An infrared gas analyzer comprising:
an infrared source for emitting infrared rays;
a light sensor responsive to the quantity of light received;
means for directing some of said infrared rays through a measuring-light optical system to said light sensor, said measuring-light optical system comprising a sample cell filled with a sample gas, a first filter for principally transmitting infrared rays of a fixed wave-length band included within the absorption wave-length band of a measurement component, and a temperature compensating cell enclosing a gas which has a part of its absorption wave-length band within the transmission wave length band of said first filter but having a spectrum different from the spectrum of said measurement component; and means for directing others of said infrared rays through a reference-light optical system to said light sensor, said reference-light optical system comprising an interference cell enclosing a gas containing a fixed density of said measurement component, an interference compensating cell filled with the sample gas, and a second filter for transmitting infrared rays of a wave-length band that includes the major part of the transmission wave-length band of said first filter.

2. The infrared gas analyzer as defined in claim 1, wherein at least one of said optical systems includes a light throttle for varying the relative amounts of infrared rays through said optical systems.

3. The infrared gas analyzer as defined in claim 1, wherein said interference compensating cell is adjustable for varying the length of the path of said infrared rays through said interference compensating cell.

4. The infrared gas analyzer as defined in claim 1, wherein one end of the interference compensating cell forms a window for transmission of infrared rays, and the interference cell is inserted hermetically into the other end thereof and is movable in the direction of insertion so as to change the length of the interference compensating cell.

5. The infrared gas analyzer as defined in claim 1, further comprising a detector equipped with a metallic block in which first and second light inlet ports intersect each other, wherein a light sensor is positioned at the intersection of the two light inlet ports, and the first and second filters are attached to the metallic block to close the first and second light inlet ports respectively, and temperature control means is provided for maintaining the metallic block at a fixed temperature.

6. The infrared gas analyzer as defined in claim 3, wherein each of said light inlet ports is conical.

7. The infrared gas analyzer as defined in claim 3, wherein measuring light is introduced into the first light inlet port and reference light is introduced into the second light inlet port alternately to obtain the light sensor output, and the a-c component of the light sensor output is used as a measurement signal, while the superposed a-c and d-c components is fed as an input to the temperature control means.

8. A method of analyzing a gas to determine the density of a measurement component of the gas, said method comprising the steps of:

providing a measuring-light optical system between an infrared ray source and a light sensor, said measuring-light optical system including a sample cell, a first filter for principally transmitting infrared rays of a fixed wave-length band included within the absorption wave-length band of said measurement component, and a temperature compensating cell enclosing a gas which has a part of its absorption wave-length band within the transmission wave-length band of said first filter but has a spectrum different from the spectrum of said measurement component;

providing a reference-light optical system between said infrared ray source and said light sensor, said reference-light optical system including an interference cell enclosing a gas containing a fixed density of said measurement component, an interference compensating cell, and a second filter for transmitting infrared rays of a wave-length band that includes the major part of the transmission wavelength band of the first filter;

setting the length of the temperature compensating cell and the density of the gas therein so that, with temperature fluctuation, variations in the absorption by the temperature compensating cell within the wave-length band of said first filter equals variations in absorption by the interference cell within the wave-length band of said second filter;

introducing a gas without infrared absorption as a sample gas in both said sample cell and said interference compensating cell, and setting the relative amounts of light passing through said respective optical systems so that the difference between the quantities of light received at the sensor from said optical systems becomes a fixed value;

supplying a sample gas containing an interference component but not a measurement component as a sample gas in both said sample cell and said interference compensating cell, and setting the length of said interference compensating cell relative to said sample cell so that the difference between the quantities of light received at said sensor from said optical systems becomes said fixed value;

supplying a sample gas having an unknown density of said measurement component to both said sample cell and said interference compensating cell and detecting the difference between the quantities of light received at said light sensor from said optical systems.

* * * * *